United States Patent [19]

Russo et al.

[11] Patent Number: 4,668,225

[45] Date of Patent: May 26, 1987

[54] GASTROSTOMY TUBE AND GASTROSTOMY-JEJUNAL FEEDING TUBE COMBINATION

[75] Inventors: Ronald D. Russo, Barrington; Michael D. Caldwell, East Greenwich; Jorge E. Albina, Providence, all of R.I.

[73] Assignee: Superior Healthcare Group, Inc., Cumberland, R.I.

[21] Appl. No.: 812,924

[22] Filed: Dec. 23, 1985

[51] Int. Cl.[4] .............................................. A61M 25/00

[52] U.S. Cl. ...................................... 604/270; 604/93; 604/280; 604/285; 604/104; 604/264

[58] Field of Search ..................... 604/270, 96, 29, 48, 604/93, 280, 104, 264, 268, 275, 285, 170

[56] References Cited

U.S. PATENT DOCUMENTS

| | | | |
|---|---|---|---|
| 4,043,346 | 8/1977 | Mobley et al. | 128/343 |
| 4,311,148 | 1/1982 | Courtney et al. | 604/175 |
| 4,356,824 | 11/1982 | Vazquez | 604/35 |
| 4,390,017 | 6/1983 | Harrison et al. | 604/270 |
| 4,543,089 | 9/1985 | Moss | 604/96 |

FOREIGN PATENT DOCUMENTS

| | | | |
|---|---|---|---|
| 2125296 | 3/1984 | United Kingdom | 604/27 |

OTHER PUBLICATIONS

IVAC Rombeau TM Gastrostomy-Jejunal Feeding Tube-Model 7080.

*Primary Examiner*—Stephen C. Pellegrino
*Assistant Examiner*—John D. Ferros
*Attorney, Agent, or Firm*—Salter & Michaelson

[57] ABSTRACT

A gastrostomy-jejunal feeding tube comprises a gastrostomy tube having an enlarged resiliently, collapsible retainer element on the distal end thereof and a jejunal feeding tube which is removably received in the gastrostomy tube in a manner which allows fluids to pass through the gastrostomy tube despite the presence of the jejunal feeding tube therein. The gastrostomy-jejunal feeding tube is adapted to be installed in a patient so that the gastrostomy tube extends through the stomach wall, fascia and skin for draining fluids from the stomach and so that the jejunal feeding tube extends into the jejunum area of the intestines for feeding and medicating the patient. Since the jejunal feeding tube is removable from the gastrostomy tube it can be replaced without surgery, and since the retainer element is resiliently collapsible, it can be pulled outwardly through the stomach wall to allow the gastrostomy tube to be removed from the patient without surgery.

11 Claims, 5 Drawing Figures

GASTROSTOMY TUBE AND GASTROSTOMY-JEJUNAL FEEDING TUBE COMBINATION

BACKGROUND AND SUMMARY OF THE INVENTION

The instant invention relates to the enternal feeding of patients by tube and more particularly to a gastrostomy-jejunal feeding tube which is receivable through the wall of the stomach for feeding and medicating a patient and/or for draining fluids from the patient's stomach.

The use of feeding tubes which extend directly into the stomachs of patients is often required when patients cannot swallow or when they have strictures in their esophagi which prevent food from entering in their stomachs. In a situation of this type it is common to perform a surgical procedure known as a gastrostomy on a patient wherein an opening is formed in the skin, fascia and stomach wall and wherein a gastrostomy tube is installed in the opening to allow food and/or medication to be passed directly into the stomach and also to allow fluids to be drained therefrom. However, although a tube of this type is often necessary for draining fluids from the stomach and it can also be used for introducing feeding formula into the stomach, it has been found that it is preferable to introduce feeding formula into the jejunum portion of the intestines rather than into the stomach. Accordingly, it has been found that in many instances it is preferable to install two separate tubes in a patient, one which extends directly into the stomach for draining fluids therefrom and one which extends through the stomach and into the jejunum portion of the intestines for supplying feeding formula to the patient. However, since an installation of this type requires two semi-permanent openings in the stomach wall, fascia and skin of a patient, it has disadvantages from the standpoint of patient discomfort and it also creates additional sites for infection. In order to overcome this problem, a device known as a Rombeau tube has been used for passing feeding formula into the jejunum of a patient and also for draining fluids from the stomach through a single opening in the stomach wall, fascia and skin of the patient. In this connection, a Rombeau tube generally comprises a gastrostomy tube having an enlarged retainer portion on the distal end thereof and a jejunal feeding tube which is permanently attached to the gastrostomy tube so that it extends therethrough. A device of this type is adapted to be installed in a patient so that the gastrostomy tube portion of the device extends through the skin, fascia and stomach wall, so that the retainer portion is positioned in engagement with the inner side of the stomach wall, and so that the jejunal feeding tube portion extends through the stomach and into the jejunum. Accordingly, the gastrostomy tube portion of a Rombeau tube can be utilized for draining fluids from the stomach, whereas the jejunal feeding tube portion can be utilized for passing medication and feeding formula into the jejunum; and the entire Rombeau tube only requires a single opening in the skin, fascia and stomach wall. However, it has been found that Rombeau tubes nevertheless have several disadvantages. Specifically, it has been found that in the event that the jejunal feeding tube portion of a Rombeau tube becomes clogged with feeding formula or is other rendered inoperative, the entire Rombeau tube must be surgically replaced. Further, it has been found that although it would be preferable to install the gastrostomy tube portion of a Rombeau tube in the stomach of a patient by passing the retainer portion of the gastrostomy tube portion through a small slit or stab wound in the stomach wall and then passing the other end of the gastrostomy tube portion through a small slit or stab wound in the fascia and skin, a surgical procedure of this type is impossible since the enlarged retainer portion of the gastrostomy tube portion of a Rombeau tube cannot be easily passed through a small slit, and since the gastrostomy tube portion is permanently attached to other elements which could not be passed outwardly through a small slit in the fascia and skin. Further, it has been found that the overall surgical procedure which is required to install a Rombeau tube in a patient is made overly complicated by the cumbersome structure thereof which includes a gastrostomy tube and a jejunal feeding tube which is permanently attached to the gastrostomy tube.

The instant invention provides a highly effective feeding tube assembly which overcomes the disadvantages of utilizing separate feeding and drainage tubes, as well as the hereinabove set forth disadvantages of Rombeau tubes. Specifically, the instant invention provides a gastrostomy-jejunal feeding tube comprising a gastrostomy tube including a tubular main portion having distal and proximal ends and an enlarged retainer element on the distal end of the main portion, and a jejunal feeding tube, including a feeding tube element having distal and proximal ends and a weighted bolus on the distal end of the feeding tube element. The jejunal feeding tube is slidably and removably received in the gastrostomy tube, and it is dimensioned and configured so that fluids can pass through the gastrostomy tube despite the presence of the jejunal feeding tube therein. The gastrostomy tube and the jejunal feeding tube portions of the device are further dimensioned and configured so that they are receivable in a patient with the gastrostomy tube positioned so that it extends through the stomach wall, fascia and skin of the patient and so that the retainer element is in engagement with the inner surface of the stomach wall and with the jejunal feeding tube positioned so that the distal end thereof is received in the jejunum of the patient. In the preferred embodiment, the gastrostomy tube has a main lumen therethrough, and the jejunal feeding tube is loosely received in the main lumen so that there is sufficient clearance in the main lumen for fluids to pass therethrough around the jejunal feeding tube, and the enlarged retainer element comprises a plurality of circumferentially-spaced resilient leaves of rounded configuration which extend outwardly from the distal end of the main portion. The retainer element preferably comprises three rounded leaves or flanges, and it preferably further comprises three hub portions which extend outwardly from the main portion by a reduced amount between the leaves. The hub portions preferably extend outwardly by less than approximately 0.25 inches and preferably by approximately 0.125 inches, and the entire retainer portion is preferably integrally formed with the main portion of the gastrostomy tube from a nontoxic rubberized material such as silicone rubber. The feeding tube preferably further comprises a Y-shaped tubular element attached to the proximal end of the gastrostomy tube and the jejunal feeding tube so that one leg of the Y-shaped element communicates with the interior of the gastrostomy tube and so that the jejunal feeding tube passes through the stem of the Y-shaped element and into the other leg. For use and operation of the gastrostomy-jejunal feeding tube of the instant invention, it is preferably sugically installed in a patient by first making a working incision in the skin and fascia of the patient and then making a small slit or stab wound in the stomach wall. The distal end of the gastrostomy tube is then passed through the opening in the skin and fascia and the retainer portion is passed through the small stab wound in the stomach wall by rotating the gastrostomy tube to individually work the resilient leaves through the stab wound until the retainer portion is passed into the stomach. The leaves on the distal end are then positioned adjacent the inner surface of the stomach wall, and sutures are applied to close the stab wound in the stomach wall to secure the tube in place. A small stab wound is then made in the skin and fascia, and the proximal end of the gastrostomy tube is fed through this stab wound, and thereafter the working incision in the skin and fascia is closed and sutured. Finally, after the gastrostomy tube has been fully installed in a patient in this manner, the distal end portion of the jejunal feeding tube is passed through the gastrostomy tube and into the stomach of the patient and then into the jejunum. In this connection, the distal end of the jejunal feeding tube may be installed in the jejunum with a stylet or with an endoscopic device or it may simply be allowed to pass into the jejunum via the peristaltic action of the stomach. In any event, after the gastrostomy tube has been installed in the patient and the distal end portion of the jejunal feeding tube has been passed into the stomach, the Y-shaped element which is preferably permanently attached to the proximal end of the jejunal feeding tube is secured to the proximal end of the gastrostomy tube, and the gastrostomy tube is secured on the skin of a patient with an adhesive clamping device or the like.

After the gastrostomy-jejunal feeding tube of the instant invention has been installed in a patient in the above-described manner, the jejunal feeding tube portion thereof can be effectively utilized for passing feeding formula and medication into the jejunum in order to effectively provide nutrition and medication for the patient. The gastrostomy tube, on the other hand, can be effectively utilized for draining fluids from the stomach of the patient. However, in the event that the jejunal feeding tube portion of the assembly becomes clogged with feeding formula or is otherwise rendered inoperative, it can be withdrawn from the patient by pulling it outwardly through the gastrostomy tube so that it can easily be replaced. In this connection, if the jejunal feeding tube is of the type which has an opening which extends through the terminal end thereof, it may be advantageous to first insert a guide wire or the like into the jejunal feeding tube and to thereafter remove the feeding tube leaving the guide wire in the patient. Thereafter, a new feeding tube can easily be installed in the patient by passing it over the guide wire so that the distal end of the new tube passes into the jejunum, whereupon the guide wire can be removed. In any event, during normal operation of the feeding tube assembly of the instant invention, the leaves of the retainer portion of the gastrostomy tube effectively retain the distal end of the gastrostomy tube in a properly installed position in the stomach of the patient, and the hub portions which extend between the leaves operate to further retain the distal end of the gastrostomy tube in the stomach of the patient. The configuration of the retainer portion also enables the gastrostomy tube to be installed in the patient in the manner hereinabove set forth. Further, in the event that it becomes necessary to remove the gastrostomy tube from the patient, the leaves are collapsible so that the gastrostomy tube can be removed simply by pulling on the proximal end thereof, whereby the leaves are collapsed and pulled through the openings in the stomach wall, fascia and skin. Hence, the gastrostomy tube can be removed without an additional surgical procedure.

Accordingly, it is a primary object of the instant invention to provide an improved gastrostomy-jejunal feeding tube.

Another object of the instant invention is to provide a gastrostomy-jejunal feeding tube comprising a gastrostomy tube and a jejunal feeding tube which is removably-received in the gastrostomy tube. A still further object of the instant invention is to provide a device which can be utilized for draining fluids from the stomach and also for passing feeding formula and medication to the jejunum of a patient.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE INVENTION

Figure 1:
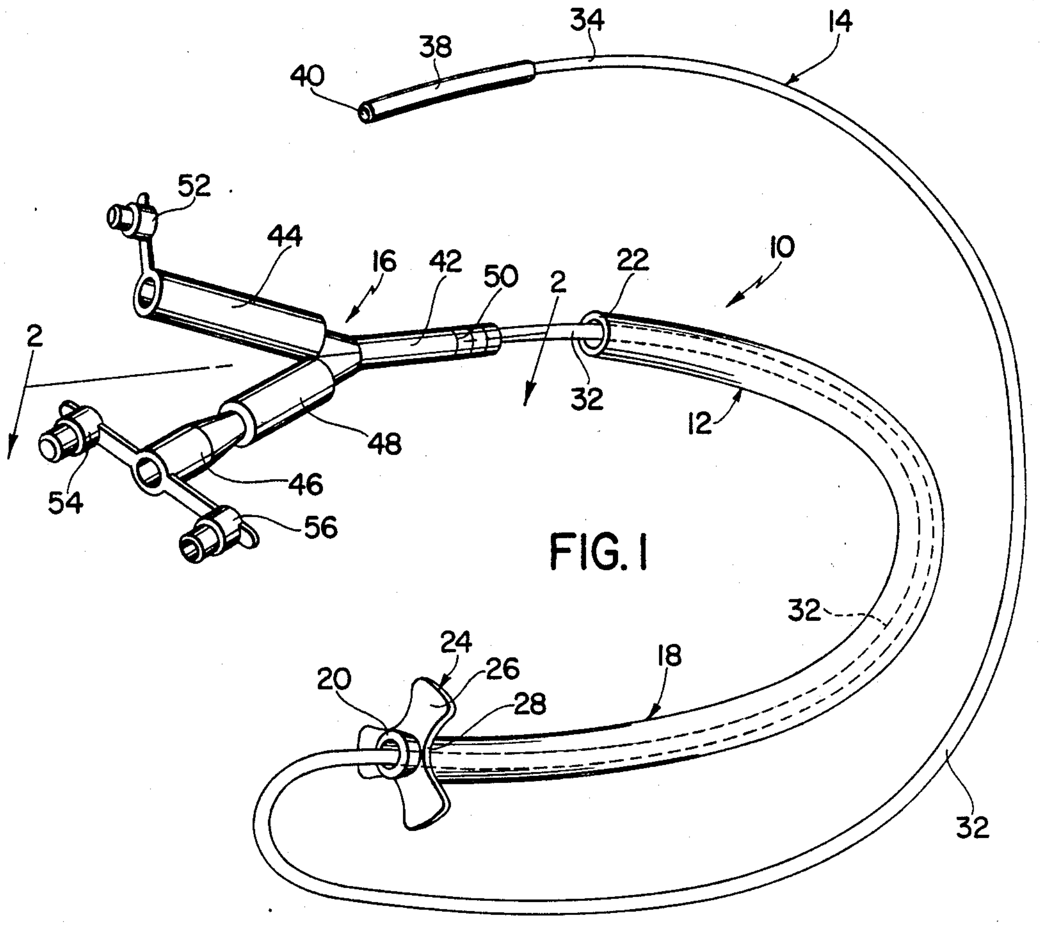
FIG. 1 is a perspective view of the gastrostomy-jejunal feeding tube of the instant invention.
Figure 2:
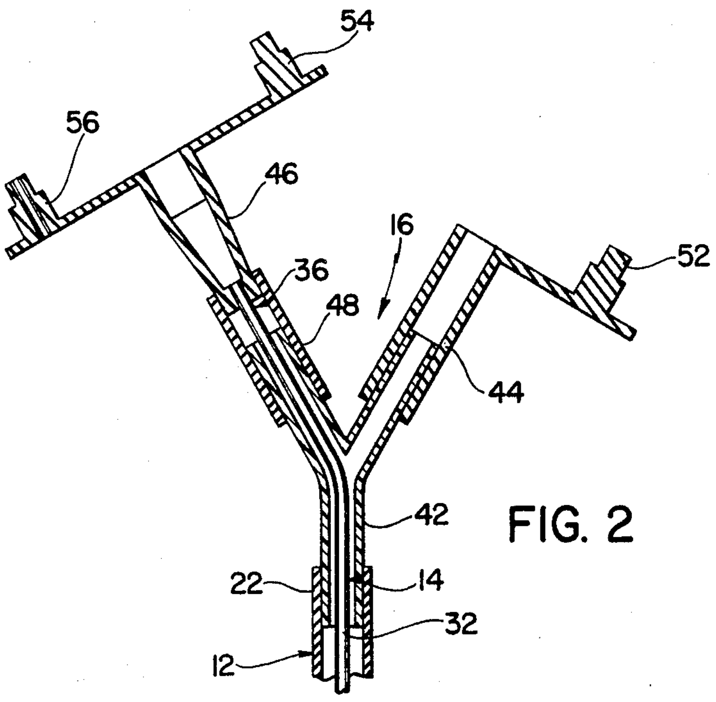
FIG. 2 is a sectional view taken along line 2—2 in FIG. 1.
Figure 3:
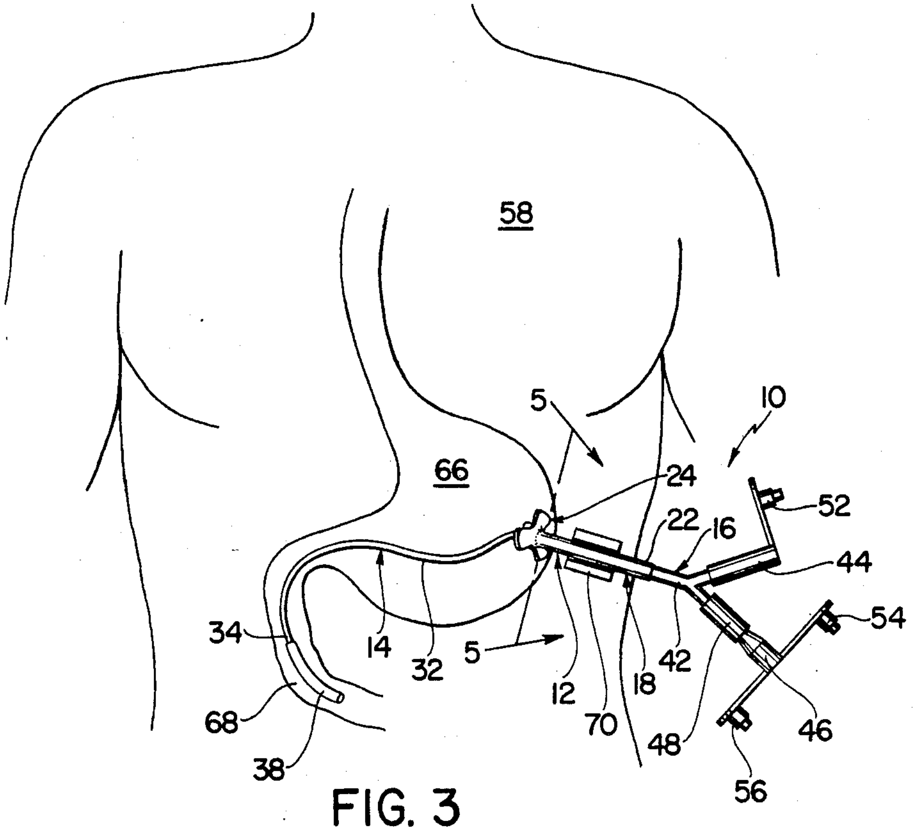
FIG. 3 is a schematic view of the gastrostomy-jejunal feeding tube installed in a patient.
Figure 4:
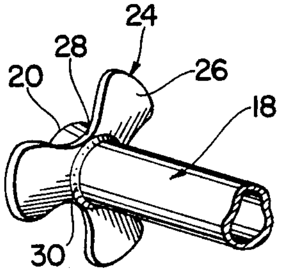
FIG. 4 is a fragmentary view of the distal end portion of the gastrostomy tube portion of the device of the instant invention.
Figure 5:
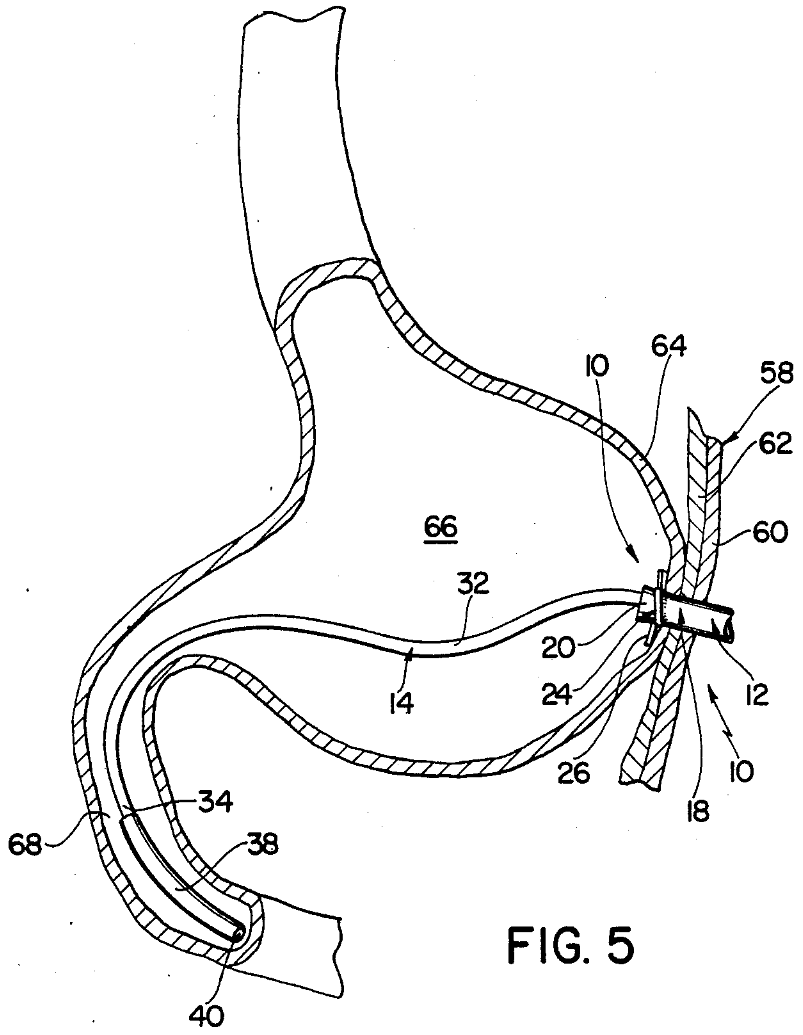
FIG. 5 is a fragmentary sectional view of the gastrostomy-jejunal feeding tube installed in the stomach of the patient.

Referring now to the drawings, the gastrostomy-jejunal feeding tube of the instant invention is illustrated in FIGS. 1–5 and generally indicated at 10 in FIGS. 1, 3 and 5. The gastrostomy-jejunal feeding tube 10 comprises a gastrostomy tube generally indicated at 12, a feeding tube generally indicated at 14, and a Y-shaped element generally indicated at 16; and it is adapted to be installed in a patient so that the gastrostomy tube 12 extends through the stomach wall, fascia and skin of the patient, and so that the jejunal feeding tube 14 extends through the gastrostomy tube 12, through the stomach, and into the jejunum area of the patient's intestines as illustrated in FIGS. 3 and 5. The Y-shaped element 16 is assembled with the gastrostomy tube 12 and the feeding tube 14 on the exterior of the body of the patient for providing access to the interiors of the gastrostomy tube 12 and the feeding tube 14.

The gastrostomy tube 12 is preferably integrally molded of a nontoxic rubberized material, such as a silicone rubber, and it preferably comprises an elongated tubular main portion 18 having a main lumen therethrough and having distal and proximal ends 20 and 22 respectively, and an enlarged retainer element generally indicated at 24 which is integrally formed with the main portion 18 adjacent the distal end 20 thereof. The main portion 18 is preferably made in a sectional dimension of approximately 28 French and a length which enables it to be installed in a patient in the manner illustrated in FIG. 3. The retainer element 24 is most clearly illustrated in FIGS. 1 and 4, and it comprises a plurality of circumferentially-spaced, collapsible leaves or flanges 26 which are preferably substantially flat and extend outwardly from the main portion 18 and a plurality of hub portions 28 which extend outwardly from the main portion 18 by a reduced amount between the leaves 26. The leaves or flanges 26 are preferably rounded at their outer extremities, and the hub portions 28 are also preferably rounded so that the hub portions 28 and the leaves 26 cooperate to define a propeller-like configuration in the retainer element 24, and the hub portions 28 preferably extend outwardly from the main portion 18 by an amount which is less than 0.25 inches and preferably by approximately 0.125 inches. Further, the entire retainer element 24 is preferably formed so that it merges with the main portion 18 in a rounded concave ring 30 which extends around the main portion 18 on the side of the retainer element 24 which faces away from the distal end 20.

The jejunal feeding tube 14 is preferably also molded of a suitable nontoxic rubberized material, such as silicone rubber, and it comprises an elongated tubular feeding tube element 32 having distal and proximal ends 34 and 36, respectively, and a weighted tubular bolus 38 which is received and secured on the distal end 34. The bolus 38 is preferably of tubular configuration so that it has an open terminal end 40 through which feeding formula from the feeding tube element 32 can pass. The feeding tube element 32 is dimensioned to be loosely received in the gastrostomy tube 12 so that fluids can pass through the interior of the jejunal feeding tube 14 and so that other fluids can pass through the main portion 18 of the gastrostomy feeding tube 12 despite the presence of the jejunal feeding tube 14 therein. More specifically, the feeding tube element 32 preferably has a sectional dimension of approximately 10 French, and it is further dimensioned so that when the gastrostomy-jejunal feeding tube assembly 10 is installed in a patient with the proximal end 36 of the feeding tube element located on the exterior of the patient's body, the bolus 38 is positionable in the jejunum area of the patient's intestines. The bolus 38 is dimensioned so that it is slidably receivable through the interior of the gastrostomy tube 12, although it may be of slightly larger dimension than the jejunal feeding tube element 32, and it preferably contains one or more weighting elements (not shown) to assure that the bolus is not expelled from the jejunum once it has been installed therein.

The Y-shaped element 16 is most clearly illustrated in FIGS. 1–3, and it is secured to the proximal end 36 of the jejunal feeding tube element 32 and the proximal end 22 of the main portion 18 of the gastrostomy tube 12. In this connection, the Y-shaped element 16 provides an effective connector for introducing fluids, such as medication and feeding formula into the jejunal feeding tube 14 and for withdrawing or draining fluids from the gastrostomy tube 12. The Y-shaped element 16 comprises a "Y" piece 42, a first tubular fitting 44 which is received on one leg of the "Y" piece 42 and a second tubular fitting 46 which is connected to the other leg of the "Y" piece 42 by means of a connector section 48. The stem of the "Y" piece 42 has a plurality of annular rings 50 formed on the exterior thereof, and it is snuggly received in the proximal end 22 of the gastrostomy tube 12. The feeding tube element 32 of the jejunal feeding tube 14 extends loosely through the stem of the "Y" piece 42 and into the leg thereof to which the second fitting 46 is secured, and the proximal end 36 of the feeding tube element 32 is snuggly received and secured in the second fitting 46. The first fitting 44 comprises a plug 52 which is receivable in the tubular interior of the first fitting 44 for providing a closure on the end thereof, and the second fitting 46 comprises a plug 54 which is receivable in the tubular interior of the fitting 46 for providing a closure on the end thereof, and an apertured plug 56 which is alternatively receivable in the tubular interior of the fitting 46 for adapting the fitting 46 to receive a "Luer" connector or the like. In any event, it is seen that when the Y-shaped element 16 is received in assembled relation with the gastrostomy tube 12 and the feeding tube 14, the second fitting 46 communicates with the interior of the jejunal feeding tube element 14 for passing fluids therethrough, whereas the first fitting 44 communicates with the interior of the gastrostomy tube 12 for draining fluids therethrough.

The use of the gastrostomy-jejunal feeding tube 10 is illustrated in FIGS. 3 and 5. As will be seen, the gastrostomy-jejunal feeding tube 10 is receivable in a patient 58 so that the distal end portion of the gastrostomy tube 12 extends through the skin 60, fascia 62 and stomach wall 64 of the patient 58 and so that the enlarged retainer portion 24 is disposed in the interior of the stomach 66 of the patient 58. More specifically, the device 10 is positionable so that the retainer element 24 engages the inner side of the stomach wall 64 and so that the feeding tube element 32 extends into the stomach 66 and into the jejunum 68 of the intestines of the patient 58. As a result, when the jejunal feeding tube 14 is installed in the patient 58 in this manner, the bolus 38 is disposed in the jejunum 68 for supplying medication and feeding formula thereto. The portion of the gastrostomy-jejunal feeding tube 10 which is disposed on the exterior of the body of the patient 58 is preferably positioned so that it extends along the surface of the body of the patient 58, and it is securable thereto by means of an adhesive clamp 70 of conventional construction. In any event, for use and operation of the gastrostomy-jejunal feeding tube 10, feeding formula or medication is introduced into the proximal end 36 of the jejunal feeding tube element 32 so that the medication or feeding formula is transmitted through the feeding tube element 32 to the jejunum 68 of the patient 58. The gastrostomy tube 12, on the other hand, can be utilized for draining fluids from the stomach 66 so that they are passed through the first fitting 44 and withdrawn from the device 10. In the event that the jejunal feeding tube 14 becomes clogged with feeding formula or is otherwise rendered inoperative, a guide wire can be installed through the jejunal feeding tube 14 so that it extends into the jejunum 68. Thereafter, the jejunal feeding tube 14 can be withdrawn from the patient 58 leaving the guide wire in the patient, and a new jejunal feeding tube can be easily installed in the patient 58 by passing it over the guide wire, through the gastrostomy tube 12 into the stomach 66 and then into the jejunum 68, whereupon the guide wire can be withdrawn leaving the new jejunal feeding tube in a properly installed position. In addition, since the leaves 26 are collapsible, it is actually possible to remove the entire device 10 from the patient 58 by first withdrawing the jejunal feeding tube 14 and then pulling on the gastrostomy tube 12 so that the leaves 26 are collapsed, and the distal end 20 of the gastrostomy tube 12 passes outwardly through the stomach wall 64, the fascia 62 and the skin 60. In this connection, under most conditions, the rim portions 28 prevent the gastrostomy tube 12 from being withdrawn inadvertently since they cooperate with the leaves for further retaining the distal end 20 in the stomach 66. However, by applying a sufficient force to the gastrostomy tube 12, the entire retaining portion 24 can be pulled through the stomach wall 64, the fascia 62 and the skin 60. The removal of the gastrostomy tube 12 in this manner is facilitated by the rounded configuration of the ring 30 on the retainer element 24.

It is seen therefore that the instant invention provides a highly effective device for feeding a patient and also for draining fluids from the stomach of the patient. The device 10 can be effectively installed in a patient in the manner hereinabove set forth; and because the jejunal feeding tube 14 is slidably received in the gastrostomy tube 12, the jejunal feeding tube 14 can be replaced without requiring an additional surgical procedure. Further, because of the configuration of the retainer element 24 on the gastrostomy tube 12, the gastrostomy tube 12 is adapted to be easily installed in a patient, and the entire gastrostomy-jejunal feeding tube 10 can be removed without a surgical procedure. Hence, it is seen that the device of the instant invention represents a significant advancement in the medical art which has merit from both a commercial standpoint and a medical standpoint.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A gastrostomy-jejunal feeding tube comprising a gastrostomy tube including a tubular main portion having distal and proximal ends and an enlarged retainer element on the distal end of said main portion, and a jejunal feeding tube including a feeding tube element having distal and proximal ends and a weighted bolus on the distal end of said feeding tube element, said jejunal feeding tube being slidably received in said gastrostomy tube, said gastrostomy tube and said jejunal feeding tube being dimensioned so that said jejunal feeding tube, including said weighted bolus thereof, can pass through said gastrotomy tube to remove said jejunal feeding tube therefrom, said gastrostomy tube and said jejunal feeding tube being further dimensioned and configured so that fluids can pass through said gastrostomy tube despite the presence of said jejunal feeding tube therein and so that said gastrostomy-jejunal feeding tube is receivable in a patient with said gastrostomy tube extending through the stomach wall, fascia and skin of the patient and said retainer element in engagement with the inner surface of the stomach wall, and with the weighted bolus of said jejunal feeding tube received in the jejunum of the patient, said enlarged retainer element comprising a plurality of resilient flanges which extend outwardly from the distal end of said main portion and a plurality of hub portions which extend outwardly from said portion by a reduced amount between said flanges.

2. In the gastrostomy-jejunal feeding tube of claim 1, said flanges further characterized as extending outwardly in circumferentially spaced relation from said main portion.

3. In the gastrostomy-jejunal feeding tube of claim 1, said flanges further characterized as being of rounded configuration.

4. The gastrostomy-jejunal feeding tube of claim 1 further characterized as comprising three of said flanges.

5. In the gastrostomy-jejunal feeding tube of claim 1, said retainer portion being integrally formed with said main portion.

6. In the gastrostomy-jejunal feeding tube of claim 5, said gastrostomy tube being integrally formed from a nontoxic rubberized material.

7. The gastrostomy-jejunal feeding tube of claim 1 further comprising a Y-shaped tubular element, the stem of said Y-shaped tubular element being attached to the proximal end of said gastrostomy tube so that one leg of said Y-shaped tubular element communicates with the interior of said gastrostomy tube, said jejunal feeding tube being received in said Y-shaped tubular element so that it passes through the stem thereof and into the other leg of said Y-shaped tubular element.

8. In the gastrostomy-jejunal feeding tube of claim 1, said hub portions extending outwardly from said main portion by less than approximately 0.25 inches.

9. In the gastrostomy-jejunal feeding tube of claim 8, said hub portions extending outwardly by approximately 0.125 inches.

10. In the gastrostomy-jejunal feeding tube of claim 1, said flanges further characterized as being substantially flat.

11. A gastrostomy tube comprising a tubular main portion having distal and proximal ends and an enlarged retainer element on the distal end of said main portion, said gastrostomy tube being dimensioned and configured so that fluids can pass therethrough and so that it is receivable in a patient with said gastrostomy tube extending through the stomach wall, fascia and skin of the patient and with said enlarged retainer element in engagement with the inner surface of the stomach wall, said enlarged retainer element comprising a plurality of resilient flanges which extend outwardly from the distal end of said main portion and a plurality of hub portions which extend outwardly from said main portion by a reduced amount between said flanges.

* * * * *